United States Patent
O'Neil et al.

(10) Patent No.: US 10,398,417 B2
(45) Date of Patent: Sep. 3, 2019

(54) SYSTEMS AND METHODS FOR MANUFACTURING CUSTOM SURGICAL INSTRUMENTS

(71) Applicant: DePuy Synthes Products, Inc., Raynham, MA (US)

(72) Inventors: Michael J. O'Neil, West Barnstable, MA (US); Robert Sommerich, Norton, MA (US); Roman Lomeli, Plymouth, MA (US)

(*) Notice: Subject to any disclaimer, the term of this patent is extended or adjusted under 35 U.S.C. 154(b) by 397 days.

(21) Appl. No.: 15/197,100

(22) Filed: Jun. 29, 2016

(65) Prior Publication Data

US 2018/0000468 A1  Jan. 4, 2018

(51) Int. Cl.
| | |
|---|---|
| A61B 17/00 | (2006.01) |
| A61B 34/00 | (2016.01) |
| A61B 90/00 | (2016.01) |
| A61B 5/0488 | (2006.01) |
| G06F 17/50 | (2006.01) |
| A61B 5/11 | (2006.01) |
| B33Y 80/00 | (2015.01) |

(52) U.S. Cl.
CPC .............. *A61B 17/00* (2013.01); *A61B 34/00* (2016.02); *A61B 90/06* (2016.02); *A61B 5/0488* (2013.01); *A61B 5/1125* (2013.01); *A61B 5/1126* (2013.01); *A61B 34/74* (2016.02); *A61B 2017/0042* (2013.01); *A61B 2017/0046* (2013.01); *A61B 2017/00424* (2013.01); *A61B 2017/00526* (2013.01); *A61B 2090/061* (2016.02); *A61B 2090/065* (2016.02); *A61B 2562/0219* (2013.01); *A61B 2562/0247* (2013.01); *B33Y 80/00* (2014.12); *G06F 17/50* (2013.01)

(58) Field of Classification Search
None
See application file for complete search history.

(56) References Cited

U.S. PATENT DOCUMENTS

| | | | | |
|---|---|---|---|---|
| 8,898,043 | B2* | 11/2014 | Ashby | A61B 34/10 |
| | | | | 382/131 |
| 9,715,563 | B1* | 7/2017 | Schroeder | A61F 2/30 |
| 2004/0243481 | A1* | 12/2004 | Bradbury | G16H 50/50 |
| | | | | 705/26.1 |

(Continued)

OTHER PUBLICATIONS

H. Dong, A. Barr, P. Loomer, C. LaRoche, E. Young, and D. Rempel, "The effects of periodontal instrument handle design on hand muscle load and pinch force" pp. 1123-1130, Aug. 2006.*

(Continued)

*Primary Examiner* — Kibrom K Gebresilassie
(74) *Attorney, Agent, or Firm* — Nutter McClennen & Fish LLP

(57) ABSTRACT

Systems and methods are disclosed in which customized instruments, e.g., surgical instruments, can be manufactured to provide improved ergonomics, comfort, and accuracy. Instruments can be customized based on various parameters, including a quantitative assessment of the user, desired or intended use of the instrument, user preferences, and so forth. Exemplary instrument properties which can be customized include size, geometry, durometer, mechanical assist, texture, color, markings, modulus of elasticity, sensor inclusion, sensor type, sensor feedback type, balance, finish, and weight.

26 Claims, 7 Drawing Sheets

(56) References Cited

U.S. PATENT DOCUMENTS

| | | | | |
|---|---|---|---|---|
| 2007/0093790 A1* | 4/2007 | Downey | A61B 17/00234 | 606/1 |
| 2011/0093108 A1* | 4/2011 | Ashby | A61B 19/50 | 700/103 |
| 2013/0203031 A1* | 8/2013 | Mckinnon | A61F 2/46 | 434/262 |
| 2013/0245801 A1* | 9/2013 | Schroeder | A61F 2/30 | 700/98 |
| 2013/0267975 A1* | 10/2013 | Timm | A61B 17/320068 | 606/169 |
| 2014/0200902 A1* | 7/2014 | Aram | A61B 17/155 | 705/2 |
| 2014/0263539 A1* | 9/2014 | Leimbach | A61B 17/07207 | 227/175.1 |
| 2016/0302800 A1* | 10/2016 | Song | A61B 17/157 | |
| 2017/0000552 A1* | 1/2017 | Asher | A61B 18/14 | |

OTHER PUBLICATIONS

[No Author Listed] Myo. Product Description. Retrieved as archived by the Wayback Machine on Apr. 8, 2016 for <https://thalmic.com/en/myo>, 13 pages.

Dong, H., et al., The effects of periodontal instrument handle design on hand muscle load and pinch force. J Am Dent Assoc. Aug. 2006;137(8):1123-30; quiz 1170.

Shemmell, J., et al., Neuromuscular adaptation during skill acquisition on a two degree-of-freedom target-acquisition task: isometric torque production. J Neurophysiol. Nov. 2005;94(5):3046-57. Epub Jun. 8, 2005.

Sidek, S.N., et al., Measurement system to study the relationship between forearm EMG signals and wrist position at varied hand grip force. 2012 International Conference on Biomedical Engineering (ICoBE), Feb. 27-28, 2012, Penang, pp. 169-174.

* cited by examiner

SYSTEMS AND METHODS FOR MANUFACTURING CUSTOM SURGICAL INSTRUMENTS

FIELD

Systems and methods for manufacturing custom instruments, e.g., surgical instruments, are disclosed herein.

BACKGROUND

Surgical procedures often require the use of instruments which are grasped by the user and manipulated to carry out various steps in the surgical procedure. Current industry practice is to employ a "one size fits all" approach in which all instruments of a given model or type are produced with identical handles designed for an "average" or "typical" user. This approach fails to address the many variations that exist among a user population in hand or forearm morphology and functional capabilities such as size, health, strength, range of motion, and reaction speed. For example, users with relatively small hands are often left with no choice but to use an instrument with an uncomfortably large handle. As another example, an instrument having poorly-adapted ergonomics can have defined pressure points that cause fatigue or injury with repeated use. As a result, many users find instruments difficult to use, or suffer from reduced accuracy and increased fatigue that can lead to user or patient injury, e.g., due to repetitive stress injuries.

In view of these and other challenges, there is a continual need for improved surgical instruments and systems and methods for manufacturing the same.

SUMMARY

Systems and methods are disclosed in which customized instruments, e.g., surgical instruments, can be manufactured to provide improved ergonomics, comfort, and accuracy. Instruments can be customized based on various parameters, including a quantitative assessment of the user, desired or intended use of the instrument, user preferences, and so forth. Exemplary instrument properties which can be customized include size, geometry, durometer, mechanical assist, texture, color, markings, modulus of elasticity, sensor inclusion, sensor type, sensor feedback type, balance, finish, and weight.

In some embodiments, a method for manufacturing a custom instrument, e.g., a surgical instrument, includes receiving a data set representing one or more parameters of a user; generating, with a computer system, a custom instrument handle design based on the data set; and controlling a manufacturing system based on the generated instrument handle design to produce a custom surgical instrument handle.

The method can include generating the data set by capturing an image of the user using an imaging device and extracting anthropometric data from the captured image. The anthropometric data can be anthropometric data of a hand of the user. The anthropometric data can be derived from distances between anatomical landmarks of the user identified in the captured image. The anthropometric data can include at least one of hand length, mid finger length, palm length, palm width, grip diameter, and mid finger span. The data set can include force measurements of the user. The force measurements can be indicative of at least one of the user's grip strength, torque capability, grip shape, grip location, and pressure point locations. The method can include obtaining the force measurements from at least one of a pressure sensor and an EMG sensor. The data set can include range of motion measurements of the user. The data set can include user preference information. The user preference information can indicate the user's preferences with respect to at least one of texture, modulus of elasticity, sensor inclusion, sensor type, sensor feedback type, bumps, recesses, balance point, weight, flat geometry, shape, color, finish, visual cues, size, geometry, length, diameter, durometer, mechanical assist, handedness, and modularity. The method can include receiving surgical technique information and generating the custom instrument design based on the surgical technique information. Generating the custom instrument design can include including a mechanical assistance feature in the instrument design based on a comparison between the user's force capability and a force requirement associated with an intended use of the instrument. Generating the custom instrument design can include determining general instrument sizing based on anthropometric data of the user included in the data set and based on an intended use of the instrument. Generating the custom instrument design can include locating contours along the instrument based on user grip shape information of the data set. Generating the custom instrument design can include locating stress-relief features along the instrument based on user pressure point information of the data set. Generating the custom instrument design can include balancing the weight of the instrument in accordance with user preference information of the data set. Generating the custom instrument design can include including a sensor in the instrument design configured to measure at least one of usage time and user-applied force. Generating the custom instrument design can include including in the instrument design an alert element configured to alert the user when an output of the sensor exceeds a predetermined threshold value. Producing the custom surgical instrument can include 3D printing at least a portion of the instrument in accordance with the custom instrument design. The method can include displaying an image of an intermediate instrument design, receiving user manipulations of the intermediate instrument design, and generating the custom instrument design based on said manipulations.

In some embodiments, a method for manufacturing a custom instrument, e.g., a surgical instrument, includes receiving a data set representing one or more parameters of a user, said parameters including anthropometric data of a hand of the user; generating, with a computer system, a custom instrument design based on the data set; and controlling a manufacturing system based on the generated instrument design to produce a custom surgical instrument.

In some embodiments, a system for manufacturing a custom instrument, e.g., a surgical instrument, includes an assessment system that measures one or more parameters of a user and generates a data set representing said measurements; a computer system that executes a design engine to generate a custom instrument handle design based on the data set; and a manufacturing system that produces a custom surgical instrument handle based on the custom instrument handle design.

The assessment system can include an imaging device configured to capture an image of a user and extract anthropometric data from the captured image. The anthropometric data can be anthropometric data of a hand of the user. The anthropometric data can be derived from distances between anatomical landmarks of the user identified in the captured image. The anthropometric data can include at least one of hand length, mid finger length, palm length, palm width, grip diameter, and mid finger span. The assessment system can include a test handle adapted to measure forces applied by a user thereto. The test handle can be adapted to measure at least one of the user's grip strength, torque capability, grip shape, grip location, and pressure point locations. The test handle can include at least one of a pressure sensor and an EMG sensor. The computer system can execute a user preference module that accesses or stores user preference information. The design engine can incorporate user preference information into the custom instrument design, the user preference information including the user's preferences with respect to at least one of texture, modulus of elasticity, sensor inclusion, sensor type, sensor feedback type, bumps, recesses, balance point, weight, flat geometry, shape, color, finish, visual cues, size, geometry, length, diameter, durometer, mechanical assist, handedness, and modularity. The system can include a surgical technique library that provides surgical technique information to the design engine, the design engine incorporating the surgical technique information into the custom instrument design. The design engine can include a mechanical assistance feature in the instrument design based on a comparison between the user's force capability as measured by the assessment system and a force requirement associated with an intended use of the instrument. The design engine can determine general instrument sizing based on anthropometric data of the user obtained by the assessment system and based on an intended use of the instrument. The design engine can locate contours along the instrument based on user grip shape information obtained by the assessment system. The design engine can locate stress-relief features along the instrument based on user pressure point information obtained by the assessment system. The design engine can include a sensor in the instrument design configured to measure at least one of usage time and user-applied force. The design engine can include in the instrument design an alert element configured to alert the user when an output of the sensor exceeds a predetermined threshold value. The manufacturing system can include a 3D printer. The computer system can display an image of an intermediate instrument design, receive user manipulations of the intermediate instrument design, and generate the custom instrument design based on said manipulations.

DETAILED DESCRIPTION

Systems and methods are disclosed in which customized instruments, e.g., surgical instruments, can be manufactured to provide improved ergonomics, comfort, and accuracy. Instruments can be customized based on various parameters, including a quantitative assessment of the user, desired or intended use of the instrument, user preferences, and so forth. Exemplary instrument properties which can be customized include size, geometry, durometer, mechanical assist, texture, color, markings, modulus of elasticity, sensor inclusion, sensor type, sensor feedback type, balance, finish, and weight.

Certain exemplary embodiments will now be described to provide an overall understanding of the principles of the structure, function, manufacture, and use of the systems and methods disclosed herein. One or more examples of these embodiments are illustrated in the accompanying drawings. Those skilled in the art will understand that the systems and methods specifically described herein and illustrated in the accompanying drawings are non-limiting exemplary embodiments. The features illustrated or described in connection with one exemplary embodiment may be combined with the features of other embodiments.

Figure 1:
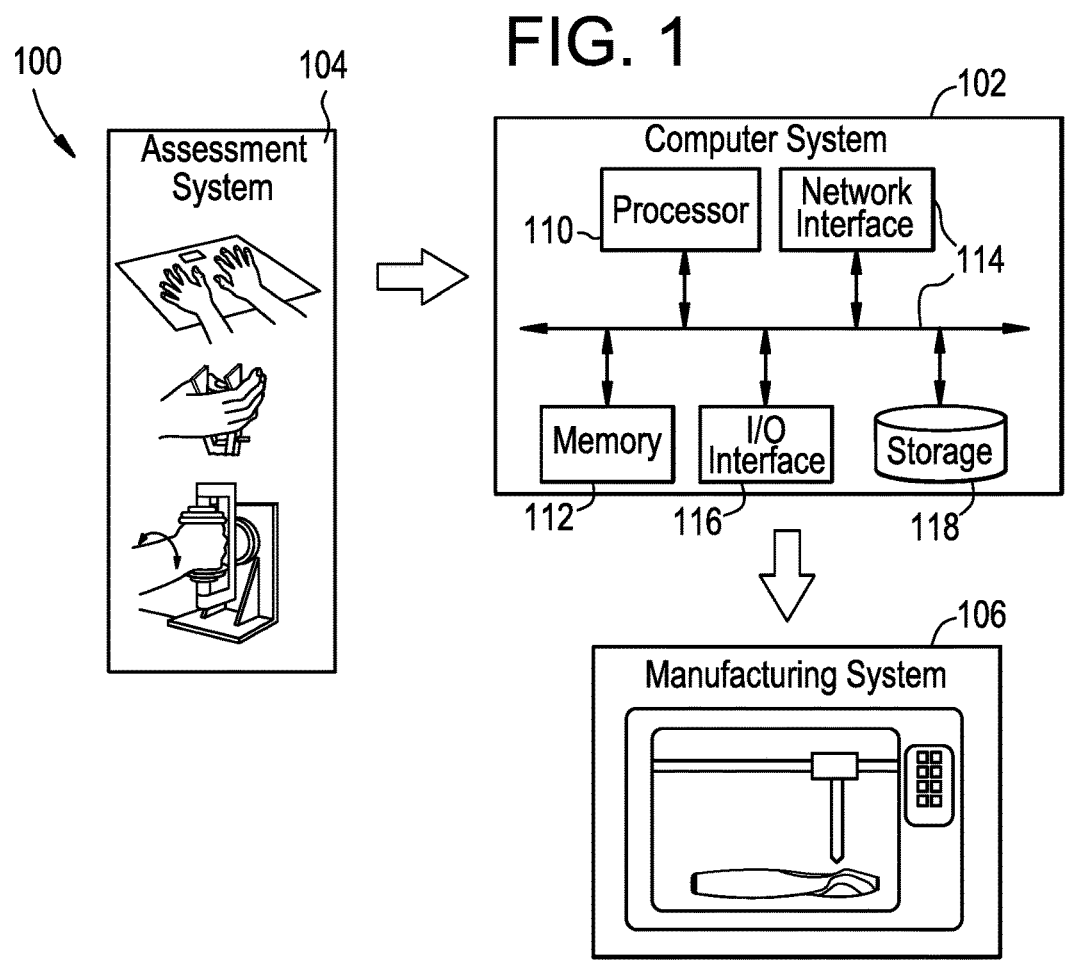
FIG. 1 is a schematic diagram of a system for manufacturing custom surgical instruments including an assessment system, a computer system, and a manufacturing system.

FIG. 1 illustrates an exemplary embodiment of a system 100 for manufacturing custom instruments, e.g., surgical instruments. As shown, the system 100 generally includes a computer system 102 that executes a software application to receive various inputs, process those inputs to generate a recommended instrument design, and to output the generated instrument design. The system 100 can include an assessment system 104 to measure one or more characteristics of a user for whom the instrument is to be designed. The system 100 can also include a manufacturing system 106 that receives an instrument design from the computer system 102 and produces a physical surgical instrument 108. The assessment system 104 and the manufacturing system 106 can be separate from the computer system 102 as shown, or can be integrated with the computer system. A user can be an individual that holds or otherwise operates the instrument. In some embodiments, the term "user" can exclude a patient on which the instrument is being used. In other embodiments, the patient can be a user.

An exemplary computer system 102 is shown in FIG. 1. While an exemplary computer system 102 is depicted and described herein, it will be appreciated that this is for sake of generality and convenience. In other embodiments, the computer system 102 may differ in architecture and operation from that shown and described here. The computer system 102 can be a tablet computer, mobile device, smart phone, laptop computer, desktop computer, cloud-based computer, server computer, and so forth. Instrument design software can execute on the computer system 102. The software can execute on a local hardware component (e.g., a tablet computer, smart phone, laptop computer, or the like) or can execute remotely (e.g., on a server or cloud-connected computing device in communications coupling with the computer system 102).

The illustrated computer system 102 includes a processor 110 which controls the operation of the computer system, for example by executing embedded software, operating systems, device drivers, application programs, and so forth. The processor 110 can include any type of microprocessor or central processing unit (CPU), including programmable general-purpose or special-purpose processors. As used herein, the term processor can refer to microprocessors, microcontrollers, ASICs, FPGAs, PICs, processors that read and interpret program instructions from internal or external memory or registers, and the like. The computer system 102 also includes a memory 112, which provides temporary or permanent storage for code to be executed by the processor 110 or for data that is processed by the processor. The memory 112 can include read-only memory (ROM), flash memory, one or more varieties of random access memory (RAM), and/or a combination of memory technologies. The various components of the computer system 102 can be interconnected via any one or more separate traces, physical busses, communication lines, etc.

The computer system 102 can also include a communication or network interface 114 and an I/O interface 116. The network interface 114 can enable the computer system 102 to communicate with remote devices (e.g., other computer systems) over a network or communications bus (e.g., a universal serial bus). The I/O interface 116 can facilitate communication between one or more input devices, one or more output devices, and the various other components of the computer system 102. Exemplary input or output devices include electronic displays, touch screens, mechanical buttons, keyboards, and pointing devices. The computer system 102 can also include a storage device 118, which can include any conventional medium for storing data in a non-volatile and/or non-transient manner. The storage device 118 can include one or more hard disk drives, flash drives, USB drives, optical drives, various media disks or cards, and/or any combination thereof and can be directly connected to the other components of the computer system 102 or remotely connected thereto, such as through the communication interface 114. The elements illustrated in FIG. 1 can be some or all of the elements of a single physical machine. In addition, not all of the illustrated elements need to be located on or in the same physical machine.

The various functions performed by the computer system 102 can be logically described as being performed by one or more modules. It will be appreciated that such modules can be implemented in hardware, software, or a combination thereof. It will further be appreciated that, when implemented in software, modules can be part of a single program or one or more separate programs, and can be implemented in a variety of contexts (e.g., as part of an embedded software package, an operating system, a device driver, a standalone application, and/or combinations thereof). In addition, software embodying one or more modules can be stored as an executable program on one or more non-transitory computer-readable storage mediums. Functions disclosed herein as being performed by a particular module can also be performed by any other module or combination of modules, and the computer system 102 can include fewer or more modules than what is shown and described herein.

Figure 2:
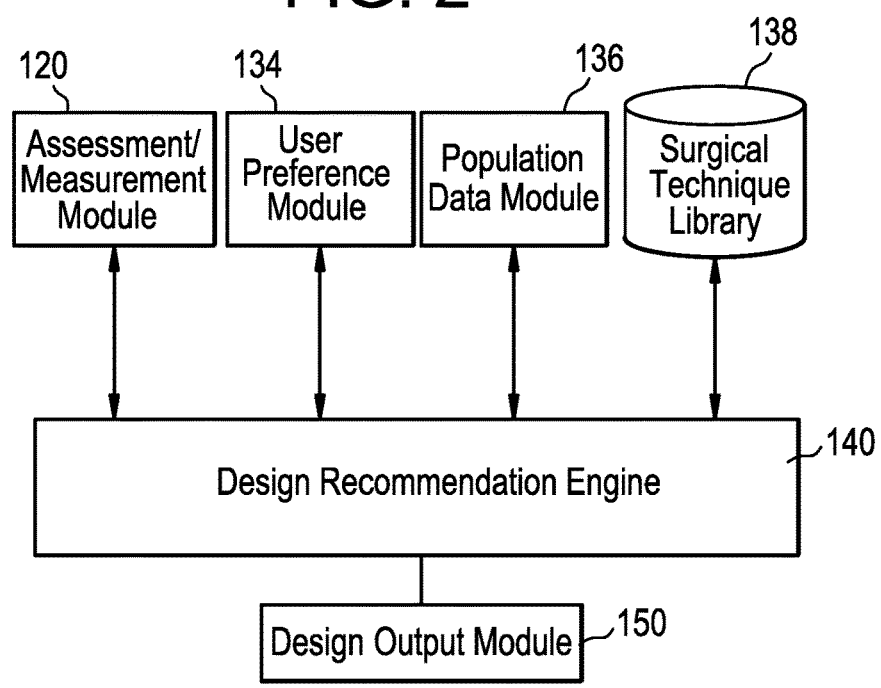
FIG. 2 is a functional architecture diagram of the computer system of FIG. 1.

FIG. 2 is a schematic diagram of the modules of one exemplary embodiment of the computer system 102. As shown, the system 100 can include an assessment or measurement module 120 that can receive inputs representative of various properties of the user for whom a custom instrument is to be designed. Exemplary inputs can include anthropometric or dimensional inputs and force inputs. The inputs can be represented in a digital data set, structure, or file. The assessment module 120 can communicate via the I/O interface 116 with the assessment system 104 to receive such inputs from the assessment system.

Figure 3:
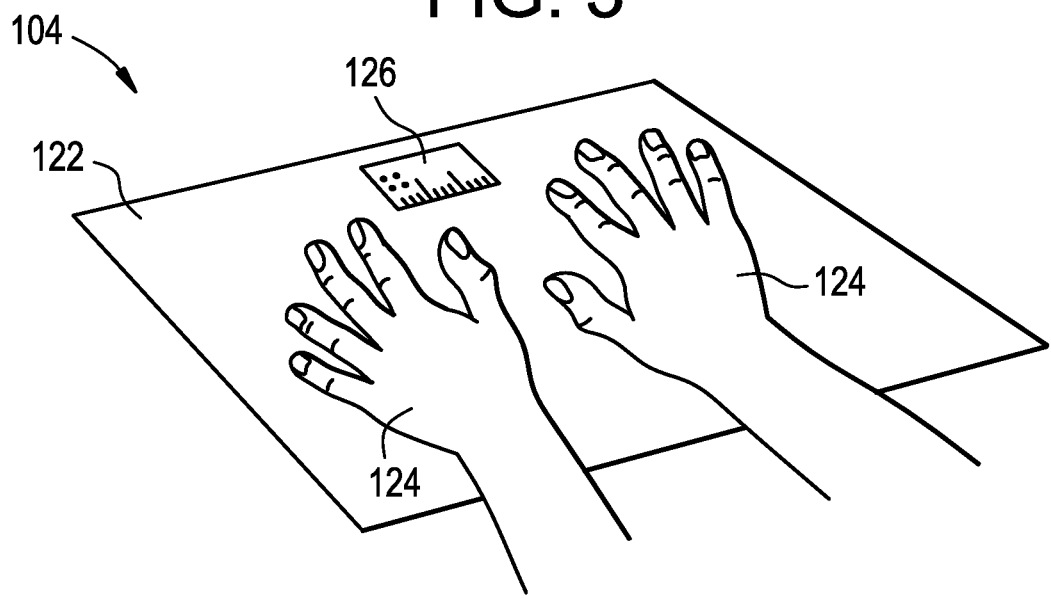
FIG. 3 is a perspective view of an imaging device of the assessment system of FIG. 1.
Figure 4:
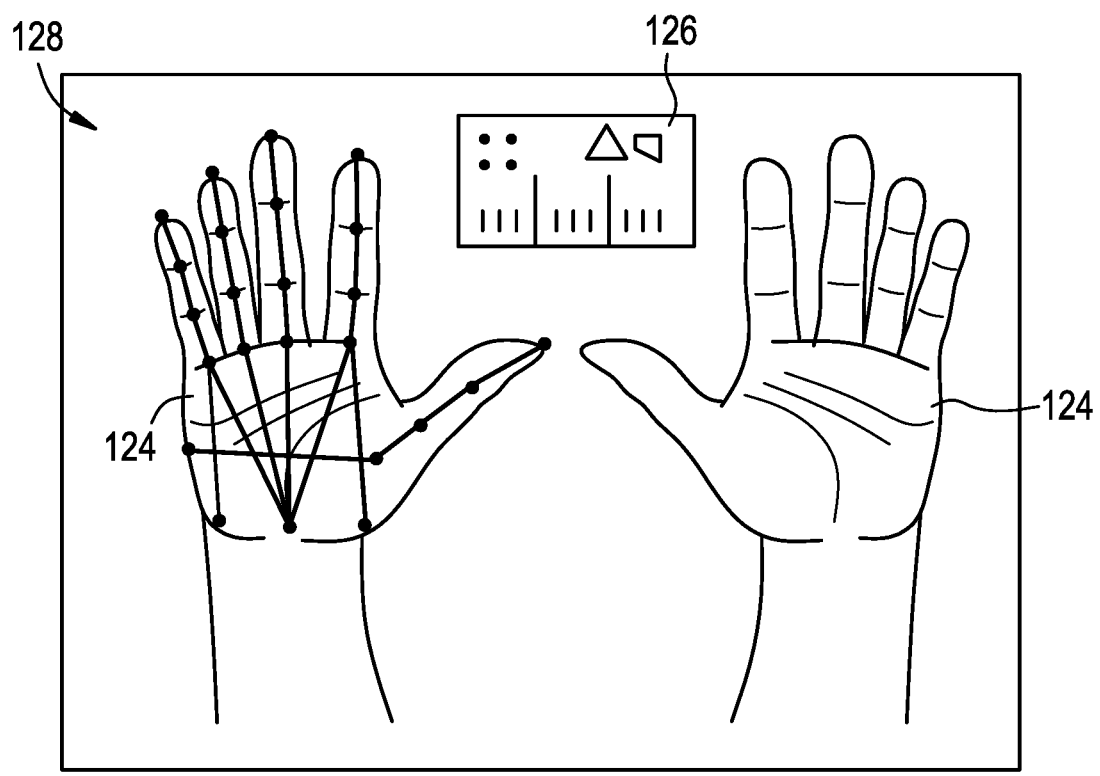
FIG. 4 is an exemplary image captured by the imaging device of FIG. 3.

The assessment system 104 can be configured to measure various properties of the user to generate input data for the assessment module 120. As shown in FIG. 3, the assessment system 104 can include an imaging device 122, e.g., an optical scanner, image sensor, camera, ultrasound imaging device, infrared imaging device, magnetic resonance imaging device, or similar. The imaging device 122 can be used to capture one or more images of the user, such as images of the user's hands 124. The images can be two- or three-dimensional images. The imaging device 122 can be a non-contact imaging device. The images can include various portions of the user, including the user's hands, wrists, and/or forearms. Images can be captured of any surface of the user's hands, including dorsal, ventral, medial, and lateral surfaces. An image processing routine can be executed by the assessment system 104 or by the computer system 102 to extract anthropometric data or other measurements from the captured image or images. A reference element 126 can be included in the field of view of the imaging device 122 having markings with dimensions or spacing known to the assessment system 104 or computer system 102, such that absolute measurements of the user can be obtained. FIG. 4 illustrates an exemplary image 128 captured using the imaging device 122 of FIG. 3. As shown, the image 128 can include the user's hands 124 and the reference element 126. The image processing routine can identify landmarks in the captured image 128 (e.g., lines in the patient's skin surface indicative of a joint of the user's hand) and can measure various distances and angles between the landmarks, as shown by the highlighted nodes and edges in FIG. 4. The assessment system 104 or computer system 102 can thus derive absolute anthropometric properties of the user from a captured image.

Figure 5:
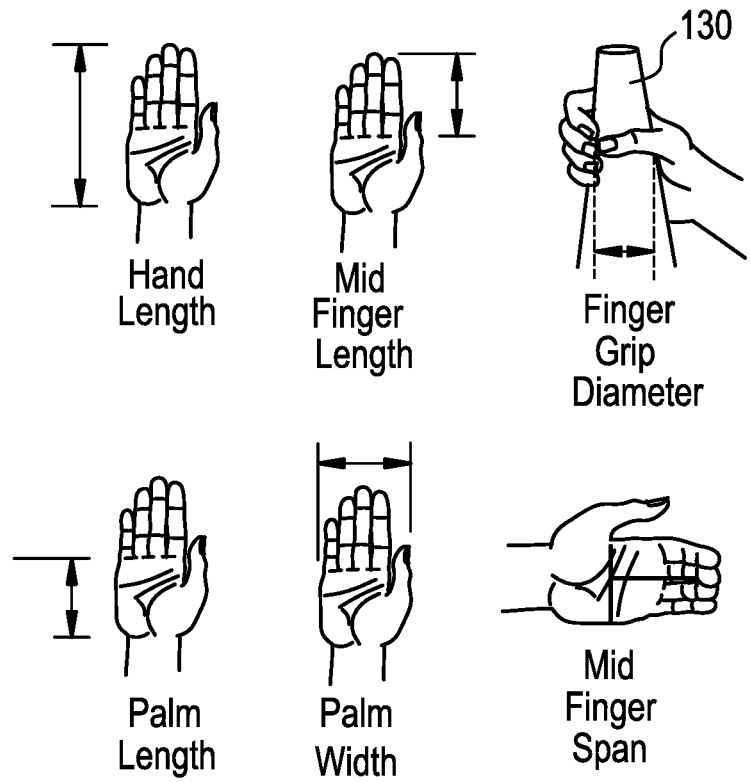
FIG. 5 is a diagram of dimensional information that can be measured by the assessment system of FIG. 1.

Exemplary anthropometric data which can be obtained by the assessment system 104 is illustrated in FIG. 5. One possible measurement can be the user's hand length, as measured from the base of the ventral surface of the palm to the tip of the longest finger. Another possible measurement can be the user's mid finger length, as measured from the base of the middle finger to the tip of the middle finger. It will be appreciated that the length of any other fingers can be measured instead or in addition. Another possible measurement can be the user's palm length, as measured from the base of the ventral surface of the palm to the base of the longest finger. Yet another possible measurement can be the user's palm width, as measured between the medial and lateral extents of the user's palm with the thumb positioned in abutment with the index finger. Other exemplary measurements can include finger width, finger length, fingertip width, fingertip length, fingertip area, hand area, hand volume, etc.

The assessment system 104 can measure the user's finger grip diameter, as shown in FIG. 5, as the diameter of a circle formed when the tip of the thumb is positioned in contact with the tip of the middle finger. Finger grip diameter can be measured using a conical measurement device 130 as shown, by inserting the conical device into the user's closed grip until the device fits snugly in the user's hand, and then measuring the location along the length of the device at which the user's hand is positioned. To facilitate such measurement, the conical device 130 can have a touch sensitive surface, a surface instrumented with contact or pressure sensors, or can have an image sensor disposed therein and reference indicia printed thereon. A similar device and technique can be used to measure mid finger span, measured as the distance between the tip of the middle finger and the ventral surface of the palm when the fingers are curled to a comfortable gripping position.

Figure 6A:
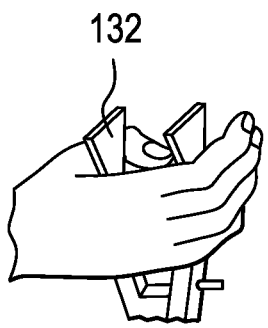
FIG. 6A is a perspective view of a force measurement device of the assessment system of FIG. 1.

As noted above, the assessment system can obtain other quantitative measurements of the user, including force or torque input measurements. To facilitate such measurement, the assessment system 104 can include a test handle adapted to be grasped and squeezed, rotated, or otherwise manipulated by the user. An exemplary force input measurement that can be captured with the assessment system 104 is the grip strength of the user. As shown in FIG. 6A, a test handle 132 can include first and second levers pivotally coupled to one another and adapted to be grasped and squeezed together by the user. The assessment system 104 can include one or more sensors (e.g., pressure sensors, transducers, strain gauges, etc.), mounted on the user, on the test handle 132, or elsewhere, for measuring a squeezing force applied to the test handle by the user. The assessment system 104 can include other types of sensors instead or in addition, such as electromyography ("EMG") sensors for measuring forces applied by the user during certain movements such as squeezing.

Figure 6B:
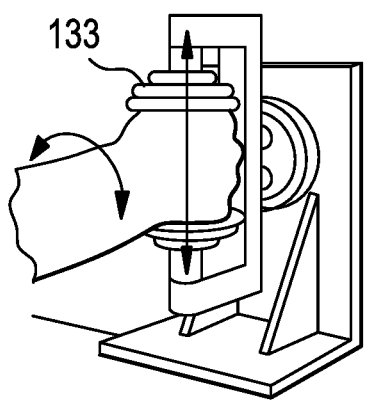
FIG. 6B is a perspective view of a torque measurement device of the assessment system of FIG. 1.

The assessment system 104 can be configured to measure input torque capabilities of the user. For example, as shown in FIG. 6B, the measuring system 104 can include a test handle 133 adapted to be grasped and/or rotated by the user. The test handle 133 can include one or more sensors for measuring the torque or force applied to the test handle by the user. In an exemplary embodiment, the test handle 133 can include a longitudinal shaft with a lever arm extending radially outward therefrom. The test handle 133 can be rotated by the user to urge the lever arm against a pressure sensor, which can measure and/or calculate the input torque or force applied by the user to the shaft. The test handle 133 can have a handle oriented perpendicular to the torque shaft as shown, or can have a handle that is oriented parallel to the torque shaft. The assessment system 104 can include other types of sensors, such as EMG sensors for measuring forces applied by the user during certain movements such as rotating or applying torque. The assessment system 104 can be configured to measure maximum torque pronation, maximum torque supination, or other torque measurements of the user. It will be appreciated that torque and grip strength can be measured using a single, combined test handle. In some embodiments, the torque measuring portion of the assessment system 104 can include a plurality of test handles, each having different sizes, shapes, or other properties. A user can interact with each of the plurality of test handles to allow the assessment system 104 to obtain a more accurate assessment of the user's torque capabilities.

The assessment system 104 can measure range of motion of the user. For example, the assessment system 104 can include a test handle with sensors that measure movement of the test handle in one or more degrees of freedom. The user can carry out maneuvers with the test handle to evaluate and quantify the user's range of motion in the one or more degrees of freedom.

The assessment system 104 can measure grip shape, grip location, and/or pressure point location. For example, the assessment system 104 can include one or more sensors (e.g., pressure sensors, transducers, strain gauges, etc.), mounted on the user, on the test handle, or elsewhere, for measuring forces at various locations on the test handle during certain user movements such as squeezing or applying torque. The assessment system 104 can include other types of sensors, such as EMG sensors for measuring forces applied at various points on the test handle. The measured data can be analyzed to identify the shape and location of the user's grip on the test handle. The measured data can also be analyzed to identify locations on the test handle where user-applied pressure peaks. The measured data can also be analyzed to determine handedness of the user (e.g., left-handed, right-handed, or ambidextrous). As discussed below, this location data can be used to inform the output instrument design, for example by locating gripping structures, finger depressions, or stress relief zones on the handle of the output instrument design.

The system 100 can include a user preference module 134 that can receive user preference information to inform the output handle design. The user preference information can be entered into the computer system 102 via a graphical user interface or can be obtained from a database or server that stores previously-entered user preference information.

The user preference module 134 can allow a user to express a preference for any of a variety of instrument design properties, which preferences can be used to inform the final output design. Exemplary user preferences can include texture, modulus of elasticity, bumps, recesses, balance point, weight, flat geometry, shape, color, finish, visual cues (e.g., markings or etch lines), size, geometry, length, diameter, durometer, mechanical assist, power assist, handedness, modularity, sensor inclusion, sensor type, sensor feedback type, and the like.

The system 100 can include a population data module 136 configured to store and analyze data for a plurality of users. The data can include assessment data, e.g., obtained by an assessment system 104, preference data, e.g., obtained by the user preference module 134, sales data, clinical data, surgical technique data, and so forth. The stored population data can be used to inform the final output design. For example, force input measurements for a population of users can be compared to repetitive stress injury data for that population to determine if a correlation exists. Instrument design can be modified in light of identified correlations to reduce future user injuries. As another example, the custom instrument can include integrated sensors configured to detect a user's input force, duration of use, or other parameters. The sensor data can be compared, e.g., by an onboard or remote processor, to the population data to determine if the user's applied force or usage time could lead to repetitive stress or other injury. The custom instrument can include means for alerting the user when such a condition is met, for example, by illuminating an LED, vibrating the instrument, or producing an audible alert.

The system 100 can include a surgical technique library 138 configured to store or access surgical technique data. The data can include information regarding the ways in which a particular instrument is designed to be used in a particular procedure, the input force requirements associated with use of an instrument in a particular procedure, and so forth. For example, in the case of a driver instrument used in implanting bone screws, the surgical technique data can include the number of screws that must be driven in a particular procedure, the input torque required to drive each bone screw, the driver length required to reach each bone screw, the drive tip required for each bone screw, etc. Instrument type or intended use information can be used to inform the final instrument design.

Figure 7:
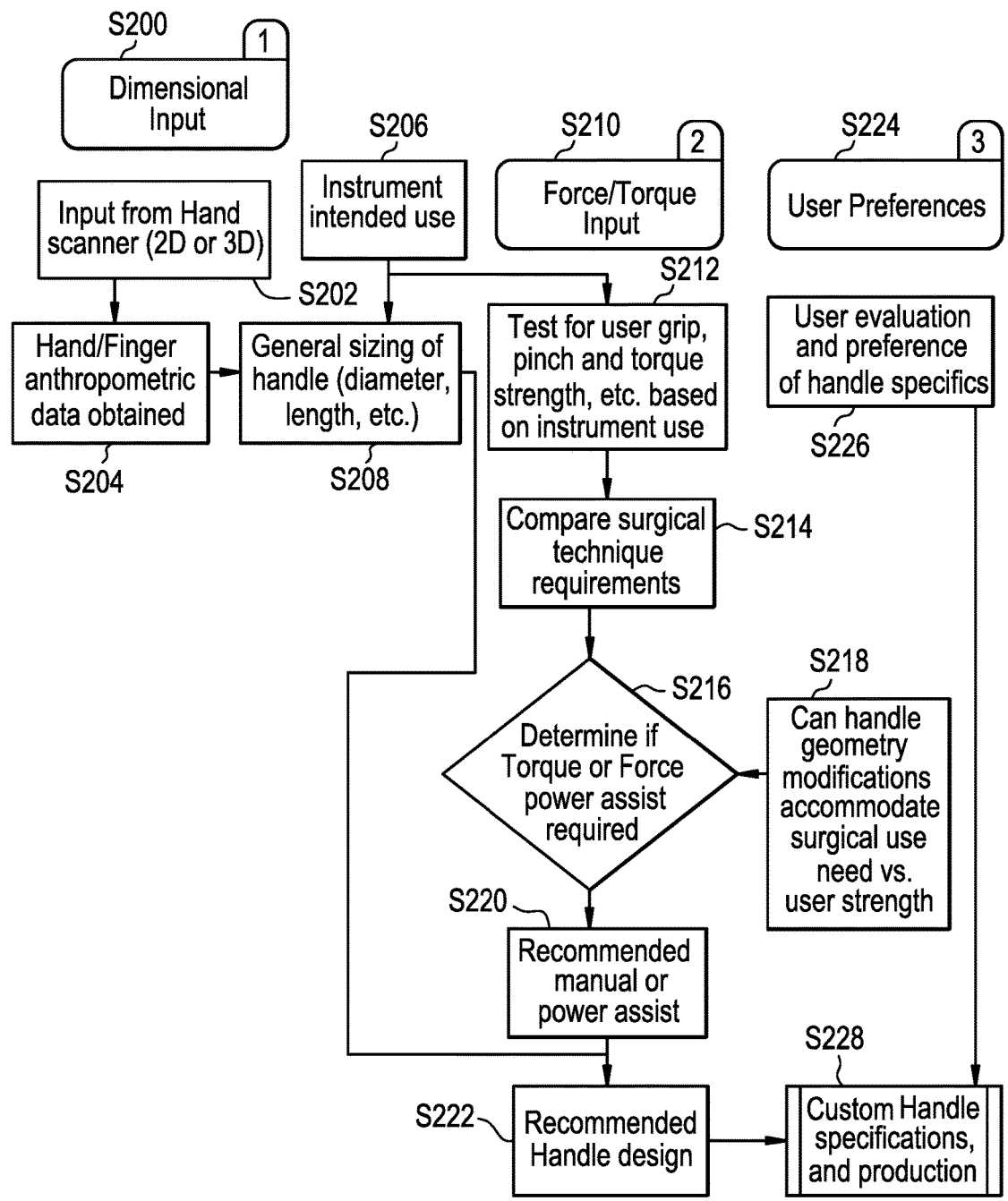
FIG. 7 is a flowchart of generating a custom instrument design.

The system 100 can include a design engine 140 configured to process various input information and to generate an output instrument design. The output design can include a customized handle. While handle customization is generally described in the examples herein, it will be appreciated that any portion of the instrument, including the entire instrument, can be customized using the systems and methods herein. Exemplary operation of the design engine 140 is illustrated in FIG. 7.

As shown, the design engine 140 can receive dimensional input from the assessment module 120 at step S200. The dimensional input can include anthropometric and other information as discussed above. For example, the design engine 140 can receive a captured image of the user at step S202 and can extract anthropometric data from the captured image at step S204. The design engine 140 can receive surgical technique information from the surgical technique library 138 at step S206. This information can include the type of instrument that is to be designed, intended use of the instrument, etc. It will be appreciated that the intended use of the instrument can have a significant impact on the instrument design. For example, an awl vs. a torque instrument vs. a rongeur can each have unique design criteria.

Figure 8:
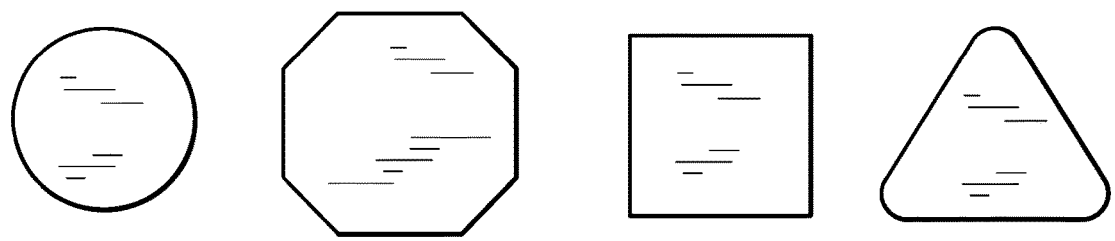
FIG. 8 is a library of exemplary instrument handle cross-sections.
Figure 9:
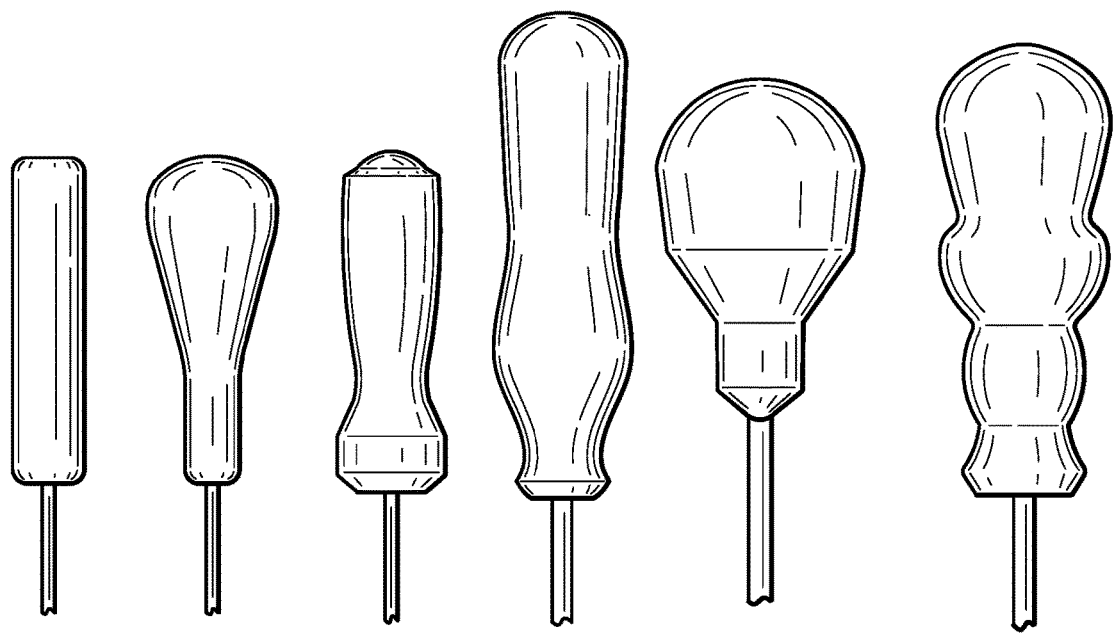
FIG. 9 is a library of exemplary instrument handle profiles.

The dimensional input and the intended use information can be used by the design engine 140 to determine general sizing of the instrument handle, e.g., the handle length and diameter, at step S208. The design engine 140 can select from a library of instrument handle cross-sections. As shown in FIG. 8, exemplary cross-sections can include circular, octagonal, square, and triangular. Any of a variety of other cross-sections can be used instead or in addition. The design engine 140 can also select from a library of instrument handle profiles. A series of exemplary handle profiles is shown in FIG. 9. The design engine 140 can select the optimal cross-section and/or profile based on the user assessment information and the intended use of the instrument.

The dimensional input can also be used to locate finger depressions, contours, or other features on the handle design, and/or to determine the handedness of the handle design.

The design engine 140 can receive force or torque input from the assessment module 120 at step S210. The force or torque input tested for can be determined at step S212 based on the intended instrument use or other surgical technique data from step S206. The force and/or torque capabilities of the user can be compared to the surgical technique requirements, as received from the surgical technique library 138, at step S214. For example, the tightening torque required for a particular procedure can be compared to the user's comfort level or capability of delivering such torque. A determination can then be made at step S216 as to whether force or torque assistance is needed to enable the user to achieve the force or torque required for the surgery. A determination can be made at step S218 as to whether a modification to the handle geometry can allow the user to provide the additional force or torque needed for the user to achieve the requirements of the surgery. If so, the design engine 140 can modify the handle design accordingly. For example, the design engine 140 can incorporate a longer lever arm into the handle design. Otherwise, a manual or power assist can be incorporated into the handle design at step S220.

Figure 10:
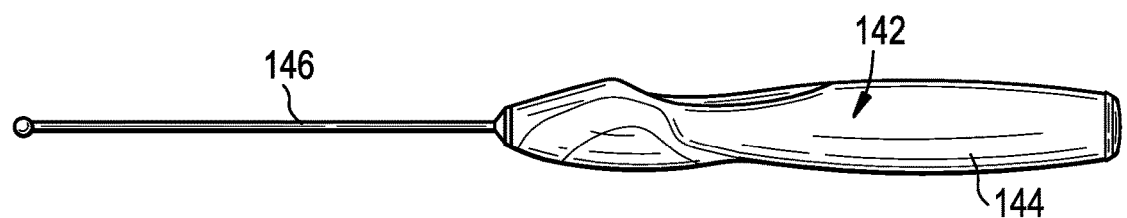
FIG. 10 is a side view of an instrument with a customized handle profile.

The force input can be used to determine the shape of the user's grip and the location of any peak pressure areas. The design engine 140 can use this information to adjust the handle profile to match the 3D shape of the user's grip. The design engine 140 can also use this information to adjust the profile, durometer, or other properties of the instrument to reduce peak stress or pressure areas. An exemplary instrument 142 having a handle 144 designed to match a user's grip shape and reduce pressure areas is shown in FIG. 10. While the handle 144 is shown with a ball tip feeler 146, it will be appreciated that the handle can be used with any of a variety of other instrument types instead or in addition, such as drivers, taps, awls, probes, rongeurs, curettes, etc. An instrument design based on dimensional input, force/torque input, and intended use or surgical technique data can be generated at step S222.

The design engine 140 can receive user preference information from the user preference module 134 at step S224. User preference information can be obtained at step S226, for example by presenting the instrument design obtained in step S222 to the user and allowing the user to manipulate or modify the design through a graphical user interface. The preference information obtained from the user preference module 134 and/or entered at step S226 can be combined with the recommended handle design of step S222 to produce a final custom handle specification at step S228.

Figure 11:
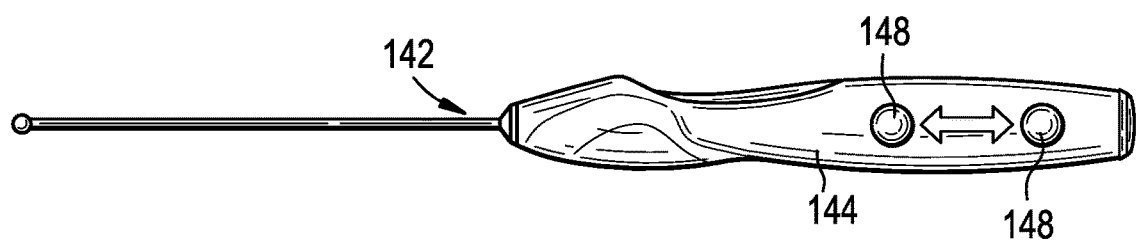
FIG. 11 is a side view of an instrument with a customized weight distribution.

An exemplary user preference can be the balance of the instrument or of the instrument handle, e.g., the longitudinal weight distribution of the instrument. As shown in FIG. 11, the design engine 140 can adjust the location of a weighted core 148 of the handle 144 based on the user preference information to achieve the user's desired balance. The balance can be changed by modifying the geometry of the instrument, the material composition of the instrument, including a separate weight component in the instrument, and so forth. For example, a weighted mass can be slidable or movable along the length of the instrument to adjust the balance of the instrument, either in use or during manufacturing.

Figure 12:
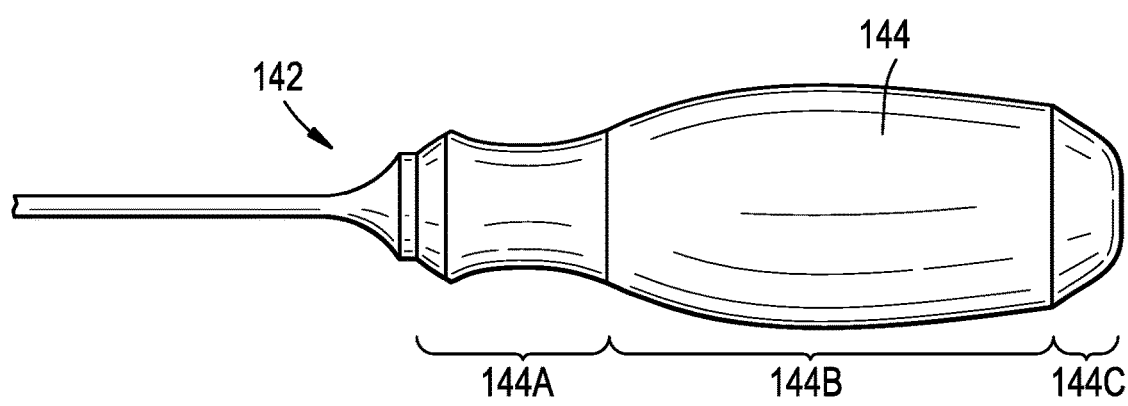
FIG. 12 is a side view of an instrument with a customized handle durometer.

Another exemplary user preference can be the durometer or hardness of the instrument. In particular, the design engine 140 can match the durometer of the handle to the user's preferred hardness. As shown in FIG. 12, the durometer of the handle 144 can be varied across a plurality of zones or regions of the handle. The illustrated handle 144 has a relatively hard distal portion 144A, a softer central portion 144B, and an even softer proximal end portion 144C. The durometer of the handle can also be adjusted based on the user's grip shape, as determined by the assessment module 120. For example, locations along the handle where the user's finger tips are disposed, or locations along the handle where peak forces are applied by the user, can be formed from a softer material to reduce pressure points and improve user comfort.

Figure 13:
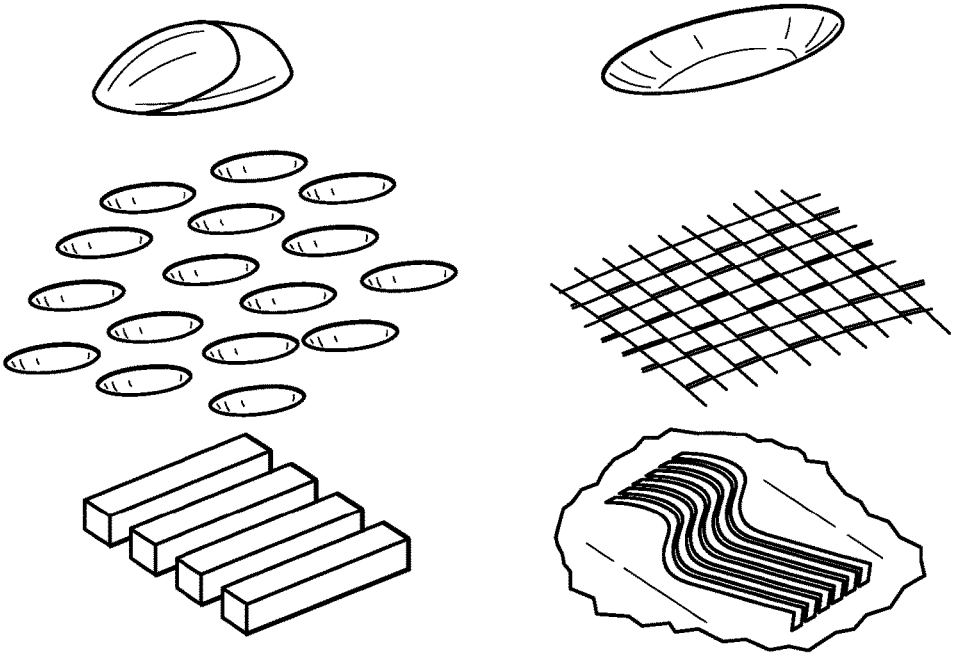
FIG. 13 is a library of exemplary instrument handle textures.
Figure 14:
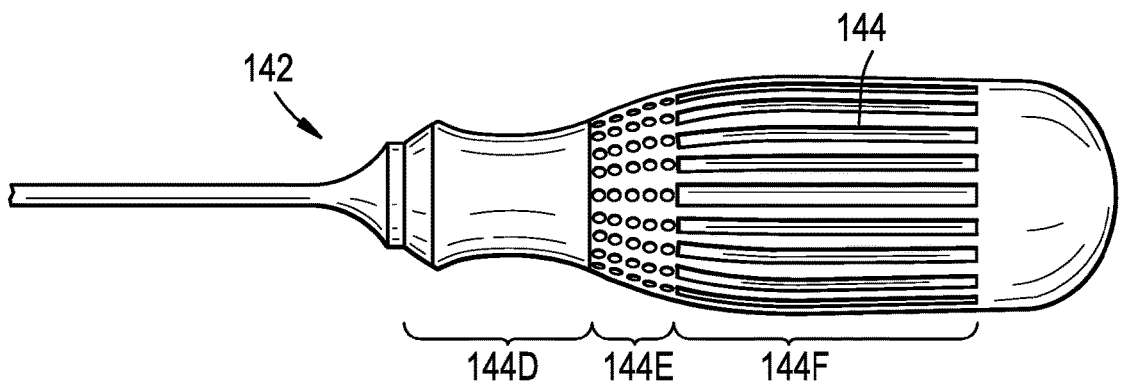
FIG. 14 is a side view of an instrument handle with a customized texture.

Another exemplary user preference can be the texture of the instrument. The design engine 140 can adjust the handle design based on the user's preferred texture, or can determine a texture based on other input data such as the shape of the user's grip and locations of peak pressure points. FIG. 13 illustrates an exemplary library of textures from which the design engine 140 can select one or more textures for use in the final handle design. As shown, exemplary textures can include raised or lowered bumps, elongate rectangular or curved ridges, alternating raised and lowered square regions, etc. As shown in FIG. 14, the texture of the handle can be varied across a plurality of zones or regions of the handle. The illustrated handle 144 has a distal portion 144D with curved, laterally-extending depressions, an intermediate nose portion 144E with a plurality of raised bumps, and a proximal portion 144F with longitudinal rectangular depressions. The texture of the handle can also be adjusted based on the user's grip shape, as determined by the assessment module 120. For example, locations along the handle where the user's finger tips are disposed, or locations along the handle where peak forces are applied by the user, can be formed with a particular texture to provide location indicators to the user or to reduce pressure points and improve user comfort. The texture of the handle can also be adjusted based on user force capabilities. For example, the design engine 140 can add more-aggressive or more-numerous gripping structures when the user's squeeze force or torque-delivery capabilities are low.

The design engine 140 can customize various other properties of the instrument based on user preferences. For example, the user's name or initials, or a hospital or other logo can be printed, etched, or otherwise formed on the handle. By way of further example, the weight of the handle can be increased or decreased based on user preference or detected user strength. As another example, the color or finish of the handle can be determined based on user preference information. If mechanical assist is indicated, the instrument design can include features for providing mechanical advantage (e.g., a gear train, a lever system, a bell crank, etc.) or features for selectively coupling the instrument to a powered driver or other instrument.

The design engine 140 can display an image of an intermediate instrument design and/or specifications for the intermediate design to give the user an opportunity to alter the design. The design engine 140 can receive user manipulations of the intermediate instrument design, and can generate a final instrument design based on said manipulations. For example, a user can interact with a graphical user interface of the computer system 102 to adjust various properties of the intermediate instrument design based on user preferences, including texture, modulus of elasticity, sensor inclusion, sensor type, sensor feedback type, bumps, recesses, balance point, weight, flat geometry, shape, color, finish, visual cues (e.g., markings or etch lines), size, geometry, length, diameter, durometer, mechanical assist, handedness, modularity, and the like.

The design engine 140 can determine whether to include a sensor in the custom instrument specification. Exemplary sensors can include force sensors, timers for measuring duration of use, counters for measuring the number of times the instrument is used, wear sensors, motion sensors, accelerometers, EMG sensors, and the like. When a user is sensitive to repetitive stress or other injury, e.g., due to a predisposition or preexisting injury, the design engine 140 can recommend inclusion of a sensor in the custom instrument design for measuring input force, pressure applied to hands, usage time, or other parameters and warning the user when measured values indicate a risk of injury. For example, the instrument can include a display, LED, light source, vibrator, speaker, or other device for providing feedback to the user when a risk of injury is detected. Whether to include a sensor, the type of sensor, feedback thresholds, and feedback type can be specified as user preference information in the user preference module 134 and can be used by the design engine 140 to inform the final instrument specification. The instrument can also be configured to alert the user when recalibration or sharpening is needed, or when instrument end-of-life is reached or approaching, for example based on a usage time sensor or usage count sensor.

The system 100 can include a design output module 150 that outputs the final instrument design as determined by the design engine 140. The final design can be output as a digital data set, structure, or file, such as a CAD file, design specification, engineering drawing, manufacturing print, template, or the like.

The system 100 can include a manufacturing system 106. The manufacturing system 106 can receive the final handle design from the output module 150 and produce a physical instrument 108 based on the design. For example, the manufacturing system 106 can produce a complete instrument or a customized handle or other sub-component of a complete instrument. Exemplary manufacturing systems 106 can include 3D printers, additive manufacturing devices, injection molding devices, extrusion devices, milling devices, lathes, CNC machines, and combinations of multiple of such devices.

The output handle design can be modular, in that the handle can include features for selectively coupling the handle to any of a variety of instruments, e.g., instruments having different types, functions, etc. For example, the handle can include a recess with one or more flats configured to selectively receive the proximal end of any of a plurality of instrument shafts.

The modular handle can be a disposable component designed for use only with a single patient or only in a single procedure. By making the handle disposable, the handle can be manufactured with features that may have otherwise been avoided due to difficulty in cleaning or sterilizing. As an example, deeper grooves or more-aggressive gripping structures can be used.

The systems and methods herein can be used to inform device selection, design, or recommend power augmentation based upon a user's dynamic strength and dexterity for various surgical steps or procedures.

Clinician morphometric (e.g., hand and arm shape and size), range of motion, electromyography (e.g., electrical muscle activity), and ergonomic data (e.g., squeeze force and pinch points) can be obtained by various means including non-contact 3D scanning of the arm and hand, EMG monitoring during key movements, including squeezing, as well as force and/or positional sensors on/or within test handles. Obtained data can be utilized to compile ideal 3D geometry of the instrument shaft or handle and/or other device based upon the specific clinician morphometry, ergonomics, and functional capabilities for devices and/or procedure. Recommendations for use of power augmentation can be included based upon clinician strength, range of motion, and instrument or device to be utilized. Surgeon strength and preference can also be used to determine the ideal durometer or other properties of the handle.

Individual dimensional data can be collected through images of a user's hand and a reference object of known size. The dimensional data can be captured with a photocopier, scanner, camera, or other image capturing device. Once an image is captured the image can be digitized and measured based upon key reference points. This data can then be used to identify the ideal instrument handle dimensions for that particular user.

The customized geometry can be manufactured through a variety of 3D printing technologies. The process can allow for a fast, custom fit device and/or system. Entire handles and shafts and working tips can be fabricated or sleeves can be fabricated to fit over known instrument geometries. Handles and/or sleeves can be formed from materials having varying modulus of elasticity to aid in comfort, reduced strain, and enhanced function.

Customized instruments can be offered to the market as a customer-specific set to enhance the surgical experience, comfort, fit, and accuracy.

Handles or instruments can be modular to assemble onto base geometries or fabricated entirely. Handles or instruments can be color coded to the procedure, to the clinician, and/or to hospital desires, and can include printed logos specific to the clinician, the procedure and/or the hospital.

Customized handles can be printed in a disposable material and mated to either reusable or disposable shafts in the operating room. By making the handles single use, greater variability in the handle design can be employed, including the use of knurling, deep grooves, and other difficult to clean features.

The systems and methods herein can allow for each surgeon to create their own highly custom sets and vary those sets over time while otherwise maintaining a consistent instrument design.

A database of clinician norms can be compiled to better inform instrument design and use recommendations including use of power augmentation or navigation for various procedural steps.

The systems and methods herein can address the many variations in user/clinician forearm/hand morphology and functional capabilities, including size, muscle health/strength, range of motion and speed of reaction. This can reduce difficulty, fatigue, inaccuracy, and risk of injury for the user and the patient. The systems and methods herein can allow for speedy customization for each customer or hospital. Customized handles or devices can be manufactured by various means including 3D printing to ensure best fit and ergonomics for customers based upon scientific assessment of each clinician as well as the function of the instrument during the procedure. Potential benefits can include improved physician ergonomics with reduced user strain, improved user comfort, enhanced accuracy, and customized user instrumentation, resulting in increased customer satisfaction.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

While the systems and methods illustrated and described herein generally involve customization of surgical instruments, it will be appreciated that the systems and methods herein can be used to customize any instrument or object. For example, the systems and methods can be used to customize handles of sports equipment, computer input devices, vehicle operating controls, robotic surgical systems (including the handle(s) of a remote console portion of the robotic surgical system), and so forth. While the systems and methods illustrated and described herein generally involve customization of instruments for an individual user, they can also be used to customize an instrument to a group of users, e.g., by averaging or otherwise combining user parameters and preferences for a plurality of users.

The instruments disclosed herein and the various component parts thereof can be constructed from any of a variety of known materials. Exemplary materials include those which are suitable for use in surgical applications, including metals such as stainless steel, titanium, or alloys thereof, polymers such as PEEK, ceramics, carbon fiber, and so forth. The various components of the instruments can be rigid or flexible. One or more components or portions of the instrument can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

Although specific embodiments are described above, it should be understood that numerous changes may be made within the spirit and scope of the concepts described.

The invention claimed is:

1. A method for manufacturing a custom surgical instrument, comprising:
   capturing an optical image of an exterior of a user's hand using an imaging device;
   extracting, with a computer system, anthropometric data of the user's hand from the captured image;
   receiving, with a computer system, a data set representing one or more parameters of the user, the data set including the anthropometric data;
   generating, with a computer system, a custom instrument handle design based on the data set; and
   producing a custom surgical instrument handle by controlling a computer-aided manufacturing system based on the generated instrument handle design.

2. The method of claim 1, wherein the anthropometric data is derived from distances between anatomical landmarks of the user identified in the captured image.

3. The method of claim 1, wherein the anthropometric data comprises at least one of hand length, mid finger length, palm length, palm width, grip diameter, and mid finger span.

4. The method of claim 1, wherein the data set includes force measurements of the user.

5. The method of claim 4, wherein the force measurements are indicative of at least one of the user's grip strength, torque capability, grip shape, grip location, and pressure point locations.

6. The method of claim 4, further comprising obtaining the force measurements from at least one of a pressure sensor and an EMG sensor.

7. The method of claim 1, wherein the data set includes range of motion measurements of the user.

8. The method of claim 1, wherein the data set includes user preference information.

9. The method of claim 8, wherein the user preference information indicates the user's preferences with respect to at least one of texture, modulus of elasticity, sensor inclusion, sensor type, sensor feedback type, bumps, recesses, balance point, weight, flat geometry, shape, color, finish, visual cues, size, geometry, length, diameter, durometer, mechanical assist, handedness, and modularity.

10. The method of claim 1, further comprising receiving surgical technique information and generating the custom instrument design based on the surgical technique information.

11. The method of claim 1, wherein generating the custom instrument design comprises including a mechanical assistance feature in the instrument design based on a comparison between the user's force capability and a force requirement associated with an intended use of the instrument.

12. The method of claim 1, wherein generating the custom instrument design comprises determining general instrument sizing based on anthropometric data of the user included in the data set and based on an intended use of the instrument.

13. The method of claim 1, wherein generating the custom instrument design comprises locating contours along the instrument based on user grip shape information of the data set.

14. The method of claim 1, wherein generating the custom instrument design comprises locating stress-relief features along the instrument based on user pressure point information of the data set.

15. The method of claim 1, wherein generating the custom instrument design comprises balancing the weight of the instrument in accordance with user preference information of the data set.

16. The method of claim 1, wherein generating the custom instrument design comprises including a sensor in the instrument design configured to measure at least one of usage time and user-applied force.

17. The method of claim 16, wherein generating the custom instrument design comprises including in the instrument design an alert element configured to alert the user when an output of the sensor exceeds a predetermined threshold value.

18. The method of claim 1, wherein producing the custom surgical instrument handle comprises 3D printing at least a portion of the instrument handle in accordance with the custom instrument handle design.

19. The method of claim 1, further comprising displaying an image of an intermediate instrument design, receiving user manipulations of the intermediate instrument design, and generating the custom instrument design based on said manipulations.

20. The method of claim 1, wherein the imaging device comprises at least one of an optical scanner, an image sensor, a camera, and an infrared imaging device.

21. The method of claim 1, wherein extracting the anthropometric data comprises executing an image processing routine on the captured image.

22. The method of claim 21,
wherein capturing the optical image of the exterior of a user's hand comprises capturing a field of view including the user's hand and a reference element, and
wherein executing an image processing routine comprises deriving absolute anthropometric properties of the user by identifying landmarks in the captured image and measuring distances and angles between the landmarks with respect to the reference element.

23. A method for manufacturing a custom surgical instrument, comprising:
capturing an image of a user using an imaging device and identifying, using a computer system, exterior anatomical landmarks of the user in the captured image;
extracting, with a computer system, anthropometric data from the captured image based on distances between anatomical landmarks of the user identified in the captured image;
receiving, with a computer system, a data set representing one or more parameters of a user, said parameters including anthropometric data of a hand of the user;
generating, with a computer system, a custom instrument design based on the data set; and
producing a custom surgical instrument by controlling a computer-aided a manufacturing system based on the generated instrument design.

24. A method for manufacturing a custom surgical instrument, comprising:
receiving, with a computer system, a data set representing one or more parameters of a user including the user's force capability;
generating, with a computer system, a custom instrument handle design based on the data set, the custom instrument design including a mechanical assistance feature based on a comparison between the user's force capability and a force requirement associated with an intended use of the instrument; and
producing a custom surgical instrument handle by controlling a computer-aided manufacturing system based on the generated instrument handle design to produce a custom surgical instrument handle.

25. The method of claim 24, wherein the user's force capability is indicative of at least one of the user's grip strength, torque capability, grip shape, grip location, and pressure point locations.

26. The method of claim 24, further comprising obtaining the user's force capability from at least one of a pressure sensor and an EMG sensor.

* * * * *